United States Patent
Kawamura et al.

(10) Patent No.: US 8,555,706 B2
(45) Date of Patent: Oct. 15, 2013

(54) FALLING SPEED MEASURING SENSOR FOR FALLING BODY VISCOMETER AND FALLING SPEED MEASURING METHOD

(75) Inventors: Kimito Kawamura, Moriya (JP); Motoyuki Tagashira, Moriya (JP); Eiji Tamura, Amagasaki (JP)

(73) Assignee: Asahi Group Holdings, Ltd., Tokyo (JP)

( * ) Notice: Subject to any disclaimer, the term of this patent is extended or adjusted under 35 U.S.C. 154(b) by 280 days.

(21) Appl. No.: 13/120,978

(22) PCT Filed: Sep. 14, 2009

(86) PCT No.: PCT/JP2009/004558
§ 371 (c)(1),
(2), (4) Date: Mar. 25, 2011

(87) PCT Pub. No.: WO2010/035418
PCT Pub. Date: Apr. 1, 2010

(65) Prior Publication Data
US 2011/0174061 A1    Jul. 21, 2011

(30) Foreign Application Priority Data
Sep. 26, 2008  (JP) .................................. 2008-247238

(51) Int. Cl.
*G01N 11/00*   (2006.01)
(52) U.S. Cl.
USPC ......................................... 73/54.15; 73/54.02
(58) Field of Classification Search
USPC ...................... 73/54.01, 54.02, 54.15, 54.19
See application file for complete search history.

(56) References Cited

U.S. PATENT DOCUMENTS 3,512,396 A    5/1970    Okamoto
3,717,026 A    2/1973    Ito
(Continued)

FOREIGN PATENT DOCUMENTS

JP    48-56480    8/1973
JP    63-97845    6/1988
(Continued)

OTHER PUBLICATIONS

Machine Translation of Yamamoto et al., Blood Viscosity Measuring Method and Apparatus, JP 2006-208260 A, translated Feb. 20, 2013.*

(Continued)

*Primary Examiner* — Hezron E Williams
*Assistant Examiner* — David Z Huang
(74) *Attorney, Agent, or Firm* — Sterne, Kessler, Goldstein & Fox P.L.L.C.

(57) ABSTRACT

A novel configuration for a falling body viscometer using an electromagnetic induction sensor, wherein the time at which a falling body passes through the electromagnetic induction sensor can be specified with enhanced accuracy. This enables the falling speed of the falling body and in turn the viscosity of a fluid to be measured with increased accuracy. A falling body viscometer is provided with a first pair of coils located at the outer periphery of a measuring container so as to be separated from each other in the vertical direction, and also with a second pair of coils located at the outer periphery of the measuring container so as to be separated from each other in the vertical direction and to be located below the first coil pair, a specified distance away therefrom.

10 Claims, 8 Drawing Sheets

(56) References Cited

U.S. PATENT DOCUMENTS

| | | | |
|---|---|---|---|
| 3,772,910 A * | 11/1973 | McGinn et al. | 73/54.19 |
| 4,388,823 A | 6/1983 | Garnaud et al. | |
| 4,466,275 A * | 8/1984 | Thone | 73/54.16 |
| 4,627,272 A | 12/1986 | Wright | |
| 5,327,778 A * | 7/1994 | Park | 73/54.21 |
| 6,201,389 B1 * | 3/2001 | Apel et al. | 324/207.2 |
| 8,485,018 B2 * | 7/2013 | Kawamura et al. | 73/12.01 |

FOREIGN PATENT DOCUMENTS

| | | |
|---|---|---|
| JP | 2-45712 | 2/1990 |
| JP | 5-39424 | 6/1993 |
| JP | 8-219973 | 8/1996 |
| JP | 08-219973 | 8/1996 |
| JP | 2004-317185 | 11/2004 |
| JP | 2006-208260 | 8/2006 |

OTHER PUBLICATIONS

International Search Report for International Application No. PCT/JP2009/004558, Japanese Patent Office, mailed Dec. 1, 2009, 4 pgs.
International Search Report for PCT Application No. PCT/JP2010/003425, Japanese Patent Office, dated Aug. 17, 2010, 5 pages.
U.S. Appl. No. 13/499,565, inventors Kawamura et al., filed Mar. 30, 2012.

* cited by examiner

FALLING SPEED MEASURING SENSOR FOR FALLING BODY VISCOMETER AND FALLING SPEED MEASURING METHOD

BACKGROUND OF THE INVENTION

1. Field of the Invention

The present invention relates to a falling body viscometer for measuring a falling speed of a falling body which is caused to fall into a substance to be measured in a measuring container, and for calculating a viscosity of the measured substance based on a measured value. More particularly, the present invention relates to a technique for enhancing accuracy in a measurement of a falling speed.

2. Background

Conventionally, there is known a viscometer for causing a falling body to fall into a liquid which is to be a measuring target for a viscosity, and for calculating the viscosity of the liquid based on a falling speed of the falling body (for example, see Patent Documents 1 and 2, identified below).

In the Patent Document 1, there is employed a structure in which an almost needle-like falling body is caused to fall into a tubular measuring container, and particularly, it is used for measuring a viscosity of blood. More specifically, there is employed a structure in which a pair of electromagnetic induction sensors separated from each other vertically is attached to the tubular measuring container, there is measured a time taken for receiving a detection signal of the almost needle-like falling body through the lower electromagnetic induction sensor after receiving a detection signal of the almost needle-like falling body through the upper electromagnetic induction sensor, and a falling termination speed is detected from the time and a distance between the upper and lower electromagnetic induction sensors. The "falling termination speed" is set to be a falling speed in uniform falling in a fluid.

Moreover, the Patent Document 1 also describes the configuration for measuring a falling termination speed of an almost needle-like falling body by using a pair of electromagnetic induction sensors, and furthermore, measuring a falling acceleration of the almost needle-like falling body by using three electromagnetic induction sensors.

There is not disclosed a specific structure of the electromagnetic induction sensor described in the Patent Document 1. For example, a magnetic field is applied to a coil surrounding the measuring container, a change in a voltage based on an induced electromotive force generated in a passage of the almost needle-like falling body is determined, and a time that the voltage is maximized is defined as a time that the coil and the almost needle-like falling body (a metallic weight) are the closest to each other. Consequently, it is possible to define a time that the almost needle-like falling body passes through a position of the electromagnetic induction sensor (a coil surface).

As shown in FIG. 8, however, an actual signal output (V) contains a noise e caused by a fluctuation in a current value for applying a magnetic field or the like, and a change rate of the signal output is minimized in the vicinity of a maximum value as is illustrated in an example of a result of a measurement in which an axis of abscissa indicates a time (t) and an axis of ordinate indicates a signal output (V) of an induced electromotive force. Therefore, a value of the signal output (V) is apt to be influenced by the noise e. In other words, the value of the signal output (V) in the vicinity of the maximum value greatly reflects the noise e. For this reason, it is hard to accurately define a time T1 (time) corresponding to a position in which the signal output (V) excluding the noise e is maximized (a position for defining a distance between the upper and lower electromagnetic induction sensors), that is, a true position S1.

The axis of abscissa in a graph shown in FIG. 8 also corresponds to upper and lower positions of the almost needle-like falling body, and also represents that the signal output (V) of the induced electromotive force is gradually increased when the fall progresses so that the almost needle-like falling body approaches the position S1 with a passage of the time, and is gradually decreased apart from the position S1.

For instance, in the example of FIG. 8, the time T1 originally corresponds to the true position S1, and the output signal is maximized by the noise e at a time T2. If a position S2 corresponding to the time T2 is defined as a position (time) in which the signal output (V) is maximized, therefore, the almost needle-like falling body is regarded to pass through the electromagnetic induction sensor at the time T2 corresponding to the position S2 which is shifted from the true position S1.

In the method described above, thus, it is hard to accurately define the time that the almost needle-like falling body passes through the position of the electromagnetic induction sensor (the coil surface) in consideration of the noise e, and the time that the almost needle-like falling body passes through the position of the electromagnetic induction sensor is defined in a state in which the influence of the noise e is directly reflected with reference to only the position S2 (time T2) on a point specified as described above. Consequently, the time that the almost needle-like falling body passes through the position of the electromagnetic induction sensor is defined with a variation depending on a situation of the noise e so that a falling speed of a falling body to be measured has a variation. There is a fear that accuracy in a measurement of a viscosity obtained based on the falling speed might not be excellent.

In the case in which a measurement for a viscosity of blood is assumed, particularly, a quantity of the blood to be taken for measuring the viscosity is limited. Therefore, it is an important object to enhance accuracy in the measurement.

PATENT DOCUMENTS

Patent Document 1: Japanese Laid-Open Patent Publication No. 2006-208260
Patent Document 2: Japanese Laid-Open Patent Publication No. 8-219973

BRIEF SUMMARY OF THE INVENTION

In the invention, therefore, it is an object to propose a novel technique capable of defining a time that a falling body passes through an electromagnetic induction sensor more accurately, thereby enhancing accuracy in measurement of a falling speed of the falling body, and furthermore, accuracy in a measurement of a viscosity of a fluid in a falling body viscometer having a configuration using the electromagnetic induction sensor.

The problems to be solved by the invention have been described above and explanation will be given to means for solving the problems.

More specifically, a first aspect of the invention is directed to a falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed. The falling speed measuring sensor includes a first coil pair disposed on an outer periphery of the measuring container, separated from each other in a vertical direction and provided to have different polarities from each other; and a second coil pair disposed on the outer periphery of the measuring container, separated from each other in the vertical direction, provided to have different polarities from each other, and arranged below the first coil pair by a specified distance. Wherein it is possible to detect: (1) a first time between a time that a maximum value is taken and a time that a minimum value is taken in an electric potential generated over the first coil pair in a passage of the falling body through the first coil pair at which there is defined a coincident electric potential with a reference voltage generated over the first coil pair by an electric potential applied from a power supply to the first coil pair; and (2) a second time between a time that a maximum value is taken and a time that a minimum value is taken in an electric potential generated over the second coil pair in a passage of the falling body through the second coil pair at which there is defined a coincident electric potential with a reference voltage generated over the second coil pair by an electric potential applied from the power supply to the second coil pair. Wherein a time required from the first time to the second time can be defined as a passing time taken for a passage through the specified distance.

Moreover, a second aspect of the invention is directed to a falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed. The falling speed measuring sensor includes a first coil pair disposed on an outer periphery of the measuring container, separated from each other in a vertical direction and provided to have different polarities from each other; and a second coil pair disposed on the outer periphery of the measuring container, separated from each other in the vertical direction, provided to have different polarities from each other, and arranged below the first coil pair by a specified distance. Wherein it is possible to detect: (1) a first intermediate time between a time that a maximum value is taken and a time that a minimum value is taken in an electric potential generated over the first coil pair in a passage of the falling body through the first coil pair; and (2) a second intermediate time between a time that a maximum value is taken and a time that a minimum value is taken in an electric potential generated over the second coil pair in a passage of the falling body through the second coil pair. Wherein a time required from the first intermediate time to the second intermediate time can be defined as a passing time taken for a passage through the specified distance.

Furthermore, a third aspect of the invention is directed to a falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed. The falling speed measuring sensor includes a first coil pair disposed on an outer periphery of the measuring container, separated from each other in a vertical direction and provided to have the same polarity; and a second coil pair disposed on the outer periphery of the measuring container, separated from each other in the vertical direction, provided to have the same polarity, and arranged below the first coil pair by a specified distance. Wherein it is possible to detect: (1) a first time that a direction of a change in an electric potential of the first coil pair which is generated in a passage of the falling body through the first coil pair is inverted in the electric potential; and (2) a second time that a direction of a change in an electric potential of the second coil pair which is generated in a passage of the falling body through the second coil pair is inverted in the electric potential. Wherein a time required from the first time to the second time can be defined as a passing time taken for a passage through the specified distance.

Moreover, a fourth aspect of the invention is directed to a falling speed measuring sensor for a falling body viscometer which is utilized in the falling body viscometer for causing a falling body to fall into a measured substance accommodated in a tabular measuring container, measuring a falling speed of the falling body by means of the falling speed measuring sensor, and measuring a viscosity of the measured substance by using the falling speed. The falling speed measuring sensor includes a first coil pair disposed on an outer periphery of the measuring container, separated from each other in a vertical direction and provided to have the same polarity; and a second coil pair disposed on the outer periphery of the measuring container, separated from each other in the vertical direction, provided to have the same polarity, and arranged below the first coil pair by a specified distance. Wherein it is possible to detect: (1) a first intermediate time between times that extreme values are taken in an electric potential of the first coil pair which is generated in a passage of the falling body through the first coil pair; and (2) a second intermediate time between times that extreme values are taken in an electric potential of the second coil pair which is generated in a passage of the falling body through the second coil pair. Wherein a time required from the first intermediate time to the second intermediate time can be defined as a passing time taken for a passage through the specified distance.

Furthermore, a fifth aspect of the invention is directed to a falling body viscometer for causing a falling body to fall into a measured substance accommodated in a tubular measuring container, measuring a falling speed of the falling body by means of a falling speed measuring sensor, and measuring a viscosity of the measured substance by using the falling speed. The falling speed measuring sensor includes a first coil pair disposed on an outer periphery of the measuring container, separated from each other in a vertical direction and provided to have different polarities from each other; and a second coil pair disposed on the outer periphery of the measuring container, separated from each other in the vertical direction, provided to have different polarities from each other, and arranged below the first coil pair by a specified distance.

Moreover, a sixth aspect of the invention is directed to a falling body viscometer for causing a falling body to fall into a measured substance accommodated in a tubular measuring container, measuring a falling speed of the falling body by means of a falling speed measuring sensor, and measuring a viscosity of the measured substance by using the falling speed. The falling speed measuring sensor includes a first coil pair disposed on an outer periphery of the measuring container, separated from each other in a vertical direction and provided to have the same polarity; and a second coil pair disposed on the outer periphery of the measuring container, separated from each other in the vertical direction, provided to have the same polarity, and arranged below the first coil pair by a specified distance.

Furthermore, a seventh aspect of the invention is directed to a falling speed measuring method of causing a falling body to fall into a measured substance accommodated in a tubular measuring container and measuring a falling speed of the falling body, the method including: using a first coil pair disposed on an outer periphery of the measuring container, separated from each other in a vertical direction and provided to have different polarities from each other, and a second coil pair disposed on the outer periphery of the measuring container, separated from each other in the vertical direction, provided to have different polarities from each other, and arranged below the first coil pair by a specified distance; defining a first time between a time that a maximum value is taken and a time that a minimum value is taken in an electric potential generated over the first coil pair in a passage of the falling body through the first coil pair at which there is defined a coincident electric potential with a reference voltage generated over the first coil pair by an electric potential applied from a power supply to the first coil pair, and a second time between a time that a maximum value is taken and a time that a minimum value is taken in an electric potential generated over the second coil pair in a passage of the falling body through the second coil pair at which there is defined a coincident electric potential with a reference voltage generated over the second coil pair by an electric potential applied from the power supply to the second coil pair; defining a time required from the first time to the second time as a passing time taken for a passage through the specified distance; and defining the falling speed of the falling body based on the passing time and the specified distance.

Moreover, an eighth aspect of the invention is directed to a falling speed measuring method of causing a falling body to fall into a measured substance accommodated in a tubular measuring container and measuring a falling speed of the falling body, the method including: using a first coil pair disposed on an outer periphery of the measuring container, separated from each other in a vertical direction and provided to have different polarities from each other, and a second coil pair disposed on the outer periphery of the measuring container, separated from each other in the vertical direction, provided to have different polarities from each other, and arranged below the first coil pair by a specified distance; defining a first intermediate time between a time that a maximum value is taken and a time that a minimum value is taken in an electric potential generated over the first coil pair in a passage of the falling body through the first coil pair, and a second intermediate time between a time that a maximum value is taken and a time that a minimum value is taken in an electric potential generated over the second coil pair in a passage of the falling body through the second coil pair; defining a time required from the first intermediate time to the second intermediate time as a passing time taken for a passage through the specified distance; and defining the falling speed of the falling body based on the passing time and the specified distance.

Furthermore, a ninth aspect of the invention is directed to a falling speed measuring method of causing a falling body to fall into a measured substance accommodated in a tubular measuring container and measuring a falling speed of the falling body, the method including: using a first coil pair disposed on an outer periphery of the measuring container, separated from each other in a vertical direction and provided to have the same polarity, and a second coil pair disposed on the outer periphery of the measuring container, separated from each other in the vertical direction, provided to have the same polarity, and arranged below the first coil pair by a specified distance; defining a first time that a direction of a change in an electric potential of the first coil pair which is generated in a passage of the falling body through the first coil pair is inverted in the electric potential, and a second time that a direction of a change in an electric potential of the second coil pair which is generated in a passage of the falling body through the second coil pair is inverted in the electric potential; defining a time required from the first time to the second time as a passing time taken for a passage through the specified distance; and defining the falling speed of the falling body based on the passing time and the specified distance.

Moreover, a tenth aspect of the invention is directed to a falling speed measuring method of causing a falling body to fall into a measured substance accommodated in a tubular measuring container and measuring a falling speed of the falling body, the method including: using a first coil pair disposed on an outer periphery of the measuring container, separated from each other in a vertical direction and provided to have the same polarity, and a second coil pair disposed on the outer periphery of the measuring container, separated from each other in the vertical direction, provided to have the same polarity, and arranged below the first coil pair by a specified distance; defining a first intermediate time between times that extreme values are taken in an electric potential of the first coil pair which is generated in a passage of the falling body through the first coil pair, and a second intermediate time between times that extreme values are taken in an electric potential of the second coil pair which is generated in a passage of the falling body through the second coil pair; defining a time required from the first intermediate time to the second intermediate time as a passing time taken for a passage through the specified distance; and defining the falling speed of the falling body based on the passing time and the specified distance.

As the effect of the invention, it is possible to produce the following advantages.

More specifically, in the first aspect of the invention, the calculation is carried out by utilizing the passing time obtained based on the first and second times which are minimally influenced by noise. On the same measuring condition, therefore, a variation in a result of the measurement is lessened so that it is possible to calculate a falling speed with high accuracy in the measurement.

In the second aspect of the invention, moreover, the falling speed is calculated by utilizing the passing time obtained based on the two intermediate values. On the same measuring condition, therefore, a variation in a result of the measurement is lessened so that it is possible to calculate a falling speed with high accuracy in the measurement.

In the third aspect of the invention, furthermore, the calculation is carried out by utilizing the passing time obtained based on the first and second times which are minimally influenced by noise. On the same measuring condition, therefore, a variation in a result of the measurement is lessened so that it is possible to calculate a falling speed with high accuracy in the measurement.

In the fourth aspect of the invention, moreover, the falling speed is calculated by utilizing the passing time obtained based on the two intermediate values. On the same measuring condition, therefore, a variation in a result of the measurement is lessened so that it is possible to calculate a falling speed with high accuracy in the measurement.

In the fifth aspect of the invention, furthermore, it is possible to obtain the two extreme values, that is, the maximum value and the minimum value for signal outputs of the first and second coil pairs, respectively. By using waveforms taking the maximum and minimum values, it is possible to obtain the passing time required for the falling body to pass through the specified distance.

In the sixth aspect of the invention, moreover, it is possible to obtain the two extreme values for signal outputs of the first and second coil pairs, respectively. By using waveforms taking the two extreme values, it is possible to obtain the passing time required for the falling body to pass through the specified distance.

In the seventh aspect of the invention, furthermore, the calculation is carried out by utilizing the passing time obtained based on the first and second times which are minimally influenced by noise. On the same measuring condition, therefore, a variation in a result of the measurement is lessened so that it is possible to calculate a falling speed with high accuracy in the measurement.

In the eighth aspect of the invention, moreover, the falling speed is calculated by utilizing the passing time obtained based on the two intermediate values. On the same measuring condition, therefore, a variation in a result of the measurement is lessened so that it is possible to calculate a falling speed with high accuracy in the measurement.

In the ninth aspect of the invention, furthermore, the calculation is carried out by utilizing the passing time obtained based on the first and second times which are minimally influenced by noise. On the same measuring condition, therefore, a variation in a result of the measurement is lessened so that it is possible to calculate a falling speed with high accuracy in the measurement.

In the tenth aspect of the invention, moreover, the falling speed is calculated by utilizing the passing time obtained based on the two intermediate values. On the same measuring condition, therefore, a variation in a result of the measurement is lessened so that it is possible to calculate a falling speed with high accuracy in the measurement.

DETAILED DESCRIPTION OF THE INVENTION

Next, a mode for carrying out the invention will be described with reference to the accompanying drawings.

Figure 1:
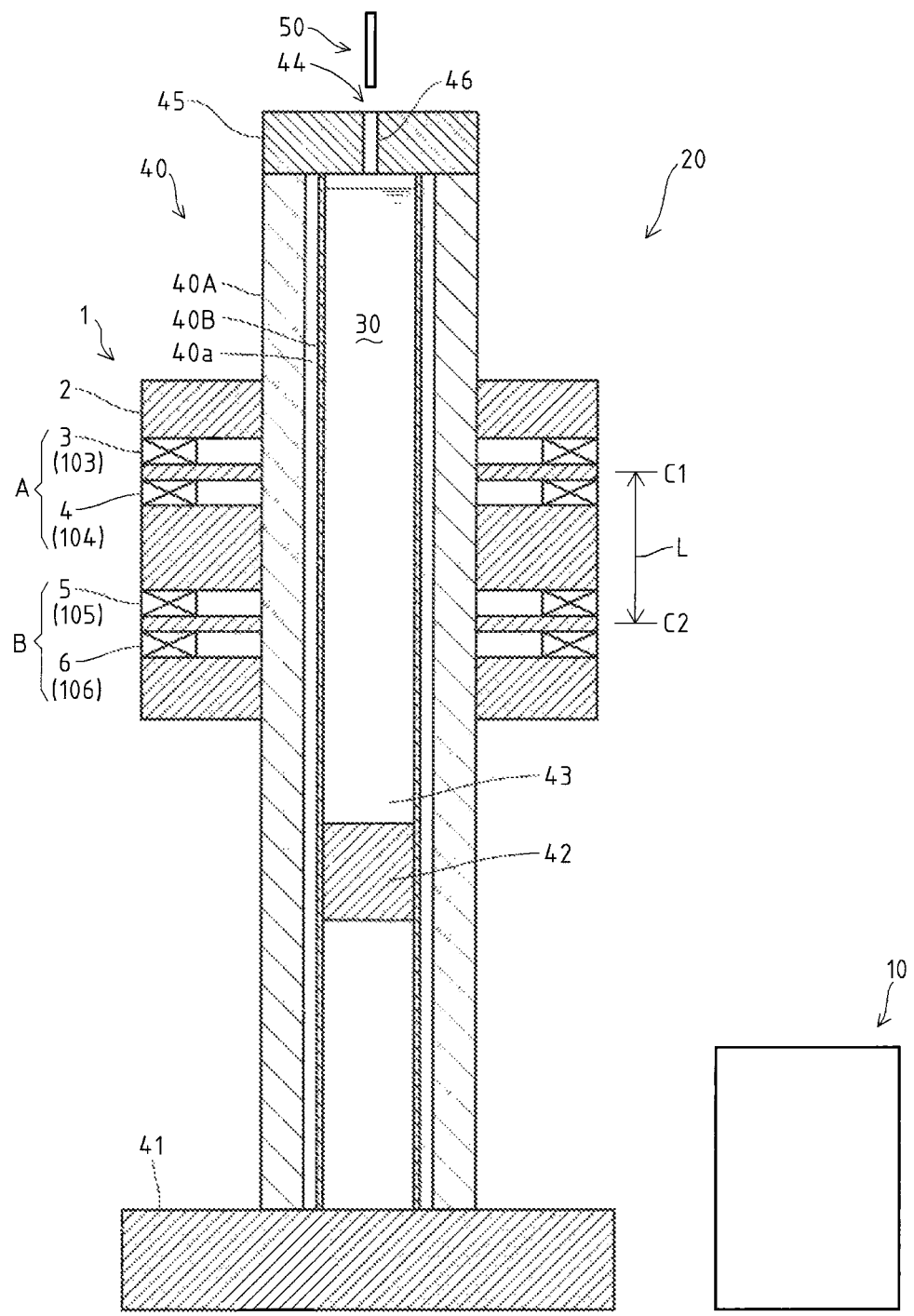
FIG. 1 is a view showing a structure of a falling body viscometer according to an embodiment of the invention.

FIG. 1 is a view for explaining a structure of a falling body viscometer 20 including a falling speed measuring sensor 1 according to an embodiment of the invention. The falling body viscometer 20 serves to cause an almost needle-like falling body 50 to fall into a measured substance 30 accommodated in a measuring container 40, to measure a falling speed of the falling body 50 by means of the falling speed measuring sensor 1, and to measure a viscosity of the measured substance 30 by using the falling speed thus measured.

The falling speed of the falling body 50 which will be described in the example represents a speed (a falling termination speed) of the falling body 50 in a fluid at a uniform speed. Moreover, various substances in which the falling body can fall by a deadweight, for example, blood, a beverage, a paint, chemicals, a yeast (a suspension or a muddy yeast), a food (a jelly food, a slurry-like food or the like), a yoghurt, a mayonnaise, a resin and the like may be the measured substance 30 and thus a measuring target for a viscosity $\mu$. In addition to a Newtonian fluid, moreover, measured substance 30 may be a substance classified as a non-Newtonian fluid. Referring to the measured substance 30, moreover, the viscosity $\mu$ can be measured for a specimen in a small quantity. In this respect, the invention particularly has advantages.

Detailed description will be given. As shown in FIG. 1, the measuring container 40 takes a tubular shape with an upper part opened, and is erected in a vertical direction with a lower part fixed to a base 41. In the measuring container 40, moreover, a plug 42 is fitted in a portion provided below a position in which the falling speed measuring sensor 1 is to be attached, and a measured object housing space 43 is formed in a space provided above the plug 42.

As shown in FIG. 1, furthermore, an inlet 44 for causing the falling body 50 to fall therein from an outside of the measured object housing space 43 is provided on a top of the measured object housing space 43. The inlet 44 is formed by providing a vertical inserting hole 46 on a cap 45 which is removably fitted into a top of the measuring container 40. Furthermore, it is desirable to have a structure in which a diameter of the inserting hole 46 is designed to be slightly greater than an outside diameter of the falling body 50 and the falling body 50 can be thus guided to fall vertically.

As shown in FIG. 1, in the measuring container 40 according to the example, two tubular containers 40A and 40B are concentrically disposed and a space 40a is formed between both of the tubular containers 40A and 40B, and a constant temperature medium (for example, water at 30° C. to 40° C., air or the like) is circulated in the space 40a so that a temperature of the measured object housing space 43 formed on an inside of the tubular container 40A can be stationary. Consequently, it is possible to cause a measuring environment to be stationary.

As shown in FIG. 1, moreover, it is desirable that the two tubular containers 40A and 40B constituting the measuring container 40 should be formed by a transparent member such as a glass or a resin. Consequently, it is possible to visually recognize a situation of an inner part of the measured object housing space 43.

As shown in FIG. 1, furthermore, the falling body 50 according to the example is constituted to be almost needle-shaped. For a material, the whole body can also be constituted by a metal and may have a structure in which a metal piece is contained in an olefin-based resin such as polyethylene or polypropylene. The falling body 50 is formed of a metal or is constituted to contain the metal in order to ensure an electrical conductivity for the following reason. More specifically, in a passage through a magnetic field formed by coils 3 and 4 and coils 5 and 6 which will be described below, an induced current is generated in the falling body 50 and a change in a magnetic field caused by the induced current is detected as a change in a voltage of each of the coils 3 and 4 and the coils 5 and 6. Several types of metal pieces for the falling body 50 can be set to have a diameter of 1 to 2 mm by a length of 3 to 8 mm. By using metal pieces having different diameters and lengths, it is possible to change the falling speed of the falling body 50, thereby distinguishing the Newtonian fluid from the non-Newtonian fluid easily.

As shown in FIG. 1, moreover, the falling speed measuring sensor 1 for measuring the falling speed of the falling body 50 falling in the measured substance 30 in the measured object housing space 43 is provided in a middle part in the vertical direction of the measuring container 40. The falling speed measuring sensor 1 has a structure in which the coils 3 and 4 and the coils 5 and 6 that function as electromagnetic induction sensors have an electrical conductivity, are made of a metal, and are provided to be separated from each other in the vertical direction in a housing portion 2 fixed to the measuring container 40 so as to surround an outer periphery of the measuring container 40. The coils 3 and 4 and the coils 5 and 6 are connected to an arithmetic and control unit 10.

As shown in FIG. 1, moreover, the coils 3 and 4 are set to be a coil pair A and an intermediate position C1 in a vertical direction thereof is defined. Similarly, the coils 5 and 6 are set to be a coil pair B and an intermediate position C2 in a vertical direction thereof is defined. An interval between the intermediate positions C1 and C2 is defined as a specified distance L. Furthermore, a central axis of each of the coil pairs A and B is disposed almost coaxially with an axis of the tubular measuring container 40 (the tubular containers 40A and 40B), and is provided on the outer periphery of the measuring container 40. Consequently, the measuring container 40 is surrounded by each of the coil pairs A and B.

As an embodiment of the structure in FIG. 1, moreover, it is also proposed that a capacity of the measured object housing space 43 is set to be 3 to 5 ml, each coil is obtained by winding a coated wire having a diameter of 0.1 mm at 30 times, a winding width is set to be 1 mm, an interval between the coils 3 and 4 is set to be 1 mm, an interval between the coils 5 and 6 is set to be 1 mm, the specified distance L is set to be 20 mm, an average diameter of each of the coils is set to be 20.5 mm, a diameter of the falling body 50 is set to be 2 mm, and a distance from a lower end of the inserting hole 46 to the intermediate position C1 is set to be 55 mm. The design of the dimension is particularly effective for measuring the viscosity $\mu$ of a measuring target to be a specimen such as blood which is limited into a small quantity. In some embodiments, the capacity of the measured object housing space 43 may be 3 ml and the coil may be obtained by winding a coated wire having a diameter of 0.05 to 0.5 mm at 10 to 50 times. Depending on the diameter of the coated wire or the number of winding operations, moreover, it is also possible to set a winding width of 0.2 to 2 mm and the intervals between the coils 3 and 4 and the coils 5 and 6 to 0.2 to 2 mm. Furthermore, it is also possible to set the specified distance L to 5 to 30 mm, the average diameter of each of the coils to 15 to 25 mm, and the distance from the lower end of the inserting hole 46 to the intermediate position C1 to 30 to 90 mm through a change in the diameter of the tubular container 40B.

Example 1

Figure 2:
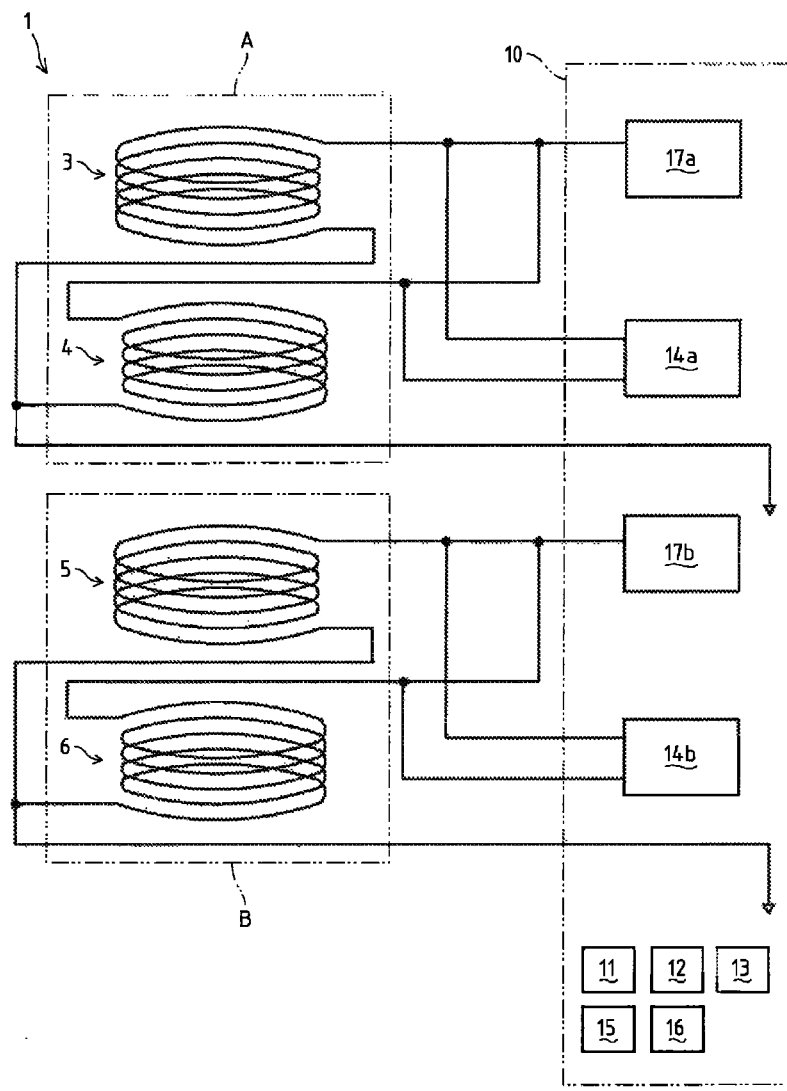
FIG. 2 is a view showing an arrangement of a coil constituting a falling speed measuring sensor according to an example 1 and a structure of an arithmetic and control unit.

Next, description will be given to an example in which the respective coil pairs A and B shown in FIG. 1 are arranged with different polarities from each other. As shown in FIG. 2, the coils 3 and 4 are disposed in such a manner that the polarities are different from each other, that is, winding directions are reverse to each other, and are connected in parallel. Similarly, the coils 5 and 6 are also disposed in such a manner that the polarities are different from each other, that is, winding directions are reverse to each other, and are connected in parallel.

As shown in FIG. 2, moreover, ends of the coils 3 and 4 and the coils 5 and 6 are connected to the arithmetic and control unit 10. The arithmetic and control unit 10 includes a CPU 11 for controlling the arithmetic and control unit 10 and a calculating portion 12 for carrying out a calculation based on a program to be executed by the CPU 11 and for obtaining a voltage value, a time or the like for each of intermediate values N1 and N2 which will be described below. Moreover, the arithmetic and control unit 10 includes a storing portion 13 for storing the intermediate values N1 and N2 which will be described below, the falling speed of the falling body 50, the program for obtaining a viscosity of the measured substance 30, a signal output (V) which will be described below, and a time (t) that the signal output (V) is detected.

Furthermore, the arithmetic and control unit 10 includes amplifying portions 14a and 14b connected to the coils 3 and 4 and the coils 5 and 6 respectively and serving to amplify electric potentials (voltages) generated over the coils 3 and 4 and the coils 5 and 6 and to output them as the signal output (V) respectively. In addition, the arithmetic and control unit 10 includes a counter 15 for defining the time (t) and outputting the time (t) to the storing portion 13. Moreover, the arithmetic and control unit 10 includes an output portion 16 for outputting a result of the calculation obtained by the calculating portion 12. Furthermore, the arithmetic and control unit 10 includes power supply portions 17a and 17b connected to the coils 3 and 4 and the coils 5 and 6 respectively and serving to generate predetermined magnetic fields. A high frequency current of 200 kHz is supplied from the power supply portions 17a and 17b to the coils 3 and 4 and the coils 5 and 6, and predetermined AC voltages generated over the coils 3 and 4 and the coils 5 and 6 are input to the amplifying portions 14a and 14b. A time resolution at 200 kHz is 50 μsec, and a lower limit value of 10 kHz is practically sufficient.

A characteristic structure shown in FIG. 2 includes the polarities (the winding directions) of the coils 3 and 4 and the coils 5 and 6, the supply of the high frequency currents from the power supply portions 17a and 17b to the coils 3 and 4 and the coils 5 and 6, the execution of an envelope detection and the amplification and output of the predetermined AC voltages generated over the coils 3 and 4 and the coils 5 and 6 respectively through the amplifying portions 14a and 14b. Other embodiments can also be implemented by using other circuit structures and other apparatus structures and the present invention is not restricted to this structure. Moreover, it is also possible to carry out a connection to hardware such as a computer or a printer, thereby executing various analyzing operations or outputting a result.

Figure 3:
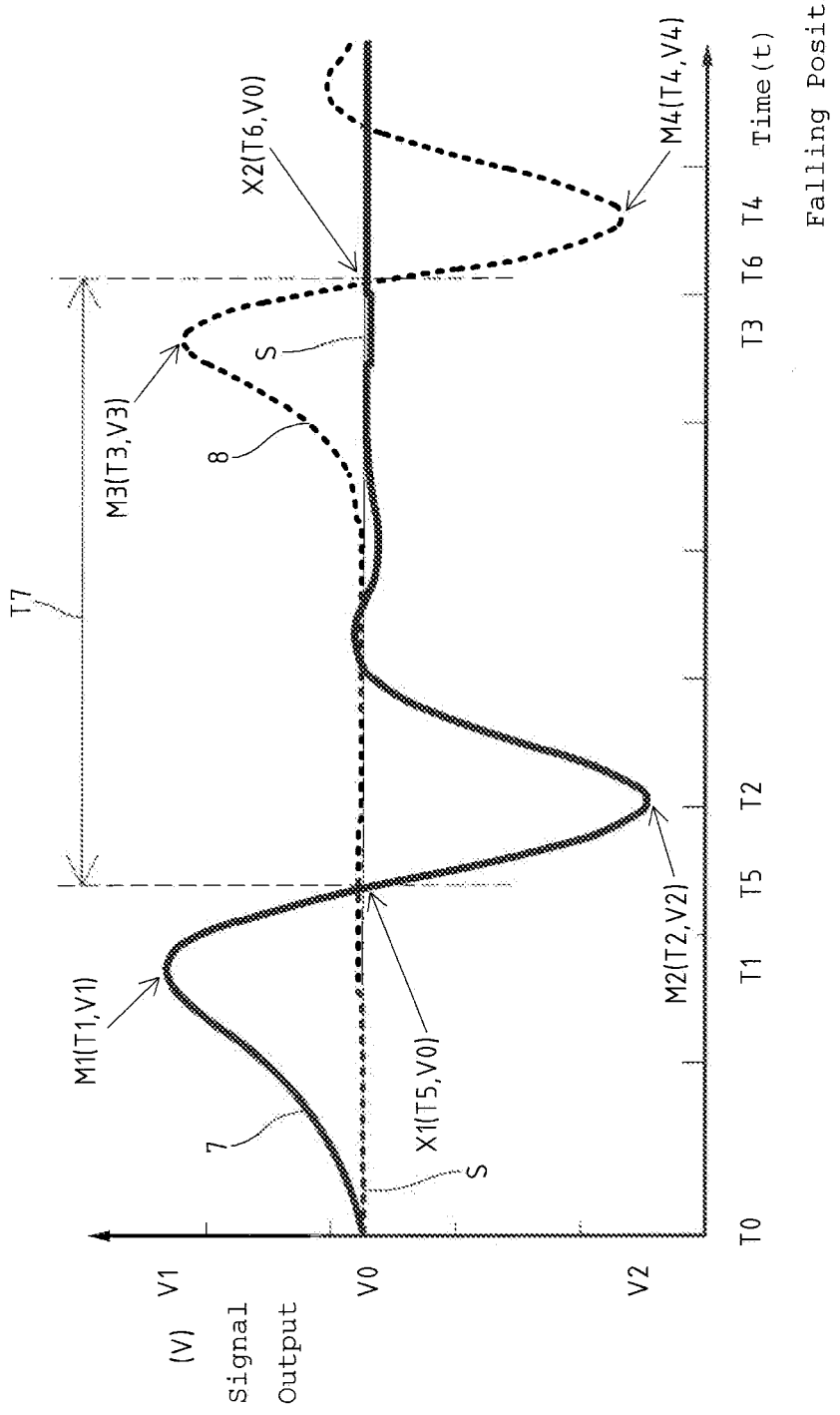
FIG. 3 is a chart showing a first example for calculating a passing time based on a waveform of a signal output (V).

Next, description will be given to a method of calculating a falling speed v of the falling body 50. FIG. 3 shows, in a waveform, the signal output (V) sent from each of the amplifying portions 14a and 14b illustrated in FIG. 2. An electric potential in each of the coils 3 and 4 shown in FIG. 2 is amplified by the amplifying portion 14a, and the signal output (V) is sent as a waveform 7 making a transition with a passage of the time (t) as shown in FIG. 3 and is stored in the storing portion 13 (see FIG. 2). Similarly, an electric potential in each of the coils 5 and 6 shown in FIG. 2 is amplified by the amplifying portion 14b, and the signal output (V) is sent as a waveform 8 making a transition with the passage of the time (t) as shown in FIG. 3 and is stored in the storing portion 13 (see FIG. 2). In FIG. 3, an axis of ordinate indicates the signal output (V) and an axis of abscissa indicates the time (t). Moreover, the axis of abscissa also corresponds to a falling position of the falling body.

First of all, as shown in FIG. 3, description will be given to the waveform 7 corresponding to the coils 3 and 4. The signal outputs (V) fluctuate with the time W. The signal output (V) is maximized at a time T1 and is minimized at a time T2. Thus, the signal output (V) is changed because an induced electromotive force is generated in the coils 3 and 4 respectively when the falling body 50 (see FIG. 1) approaches the coils 3 and 4, and the electric potentials of the coils 3 and 4 are changed by the induced electromotive force. By grasping a temporal change in the signal output (V) (the electric potential of the coil) due to the induced electromotive force, it is possible to detect a positional relationship between the coils 3 and 4 and the falling body 50.

More specifically, in FIG. 3, the signal output (V) is increased from a reference voltage V0 to a voltage V1 when the falling body 50 approaches the coil 3 from a time T0 to the time T1. The reason is as follows. When the falling body 50 approaches the coil 3, an induced current is generated in the falling body 50 and a magnetic field created by the induced current acts on the coil 3 so that the electric potential in the coil 3 is raised. On the other hand, when the falling body 50 approaches the coil 4, the signal output (V) is decreased down to a voltage V2. The reason is as follows. When the falling body 50 approaches the coil 4, a magnetic field produced by the induced current generated in the falling body 50 similarly acts on the coil 4 and a direction of the magnetic field is reverse to that acting on the coil 3 so that the electric potential in the coil 4 is lowered. The amplifying portion 14a serves to add the changes in the electric potentials generated in the coils 3 and 4 respectively, thereby outputting the serial waveform 7.

As described above, on the assumption that the coils 3 and 4 are disposed to have the different polarities from each other as shown in FIG. 2 and to continuously output the changes in the electric potentials of the coils 3 and 4, it is possible to obtain two extreme values, that is, a maximum value M1 (T1, V1) and a minimum value M2 (T2, V2) for the signal output (V) as in the waveform 7 illustrated in FIG. 3. Referring to the coils 5 and 6 shown in FIG. 2, similarly, it is possible to obtain two extreme values, that is, a maximum value M3 (T3, V3) and a minimum value M4 (T4, V4) as in the waveform 8 illustrated in FIG. 3. Although the minimum value M4 appears after the maximum value M3 in the example, it is also possible to employ a structure in which the maximum value appears after the minimum value depending on the winding direction of the coil.

As described above, as shown in FIGS. 1 to 3, the falling body viscometer 20 according to the example serves to cause the falling body 50 to fall into the measured substance 30 accommodated in the tabular measuring container 40, to measure the falling speed of the falling body 50 by means of the falling speed measuring sensor 1, and to measure a viscosity of the measured substance 30 by using the falling speed. In an exemplary embodiment, the falling speed measuring sensor 1 includes the first coil pair A (coils 3 and 4) disposed on an outer periphery of the measuring container 40, separated from each other in a vertical direction and provided to have different polarities from each other; and the second coil pair B (coils 5 and 6) disposed on the outer periphery of the measuring container 40, separated from each other in the vertical direction, provided to have different polarities from each other, and arranged below the first coil pair by a specified distance.

With the structure described above, description will be given to two examples in which the falling time of the falling body is defined.

<First Example: Example in which passing time T7 is defined based on intersecting point with reference voltage>
Next, description will be given to an example in which an intersecting point X1 of the waveform 7 between the maximum value M1 and the minimum value M2 with the reference voltage V0 and an intersecting point X2 of the waveform 8 between the maximum value M3 and the minimum value M4 with the reference voltage V0 are obtained respectively, and a time between the intersecting points X1 and X2 is defined as a passing time T7 as shown in FIG. 3.

As shown in FIGS. 2 and 3, the reference voltage V0 is obtained by applying currents to the coils 3 and 4 and the coils 5 and 6 through the power supply portions 17a and 17b respectively and measuring electric potentials as the signal output (V). The signal output (V) fluctuates by an induced electromotive force produced in the passage of the falling body 50 in the magnetic fields generated by the coils 3 and 4 and the coils 5 and 6. Although the electric potentials applied to the respective sets of the coils 3 and 4 and the coils 5 and 6 are caused to be equal to each other in the example, the electric potential applied to the coils 3 and 4 may be different from the electric potential applied to the coils 5 and 6.

As shown in FIG. 3, moreover, a point on which the waveform 7 corresponding to the coils 3 and 4 has the reference voltage V0, that is, a point on which the waveform 7 intersects with a line S of the reference voltage V0 is set to be the intersecting point X1, and a time T5 corresponding to the intersecting point X1 is defined. Similarly, a point on which the waveform 8 corresponding to the coils 5 and 6 has the reference voltage V0, that is, a point on which the waveform 8 intersects with the line S of the reference voltage V0 is set to be the intersecting point X2, and a time T6 corresponding to the intersecting point X2 is defined.

As shown in FIG. 3, furthermore, a gradient of the change in the electric potential of the signal output (V) is maximized in a time zone in the vicinity of the intersecting points X1 and X2. Even if the signal output (V) contains a noise, consequently, a variation in the electric potential which is caused by the noise is extremely smaller than a variation in the electric potential of the signal output (V) and is thus minimally influenced by the noise. In other words, on the same measuring condition, it is possible to reduce an occurrence of a variation in the positions of the intersecting points X1 and X2 (the times T5 and T6). Consequently, it is possible to ensure high accuracy in the measurement of the passing time T7 required from the intersecting point X1 to the intersecting point X2.

As shown in FIGS. 1 and 3, the time T5 of the intersecting point X1 is defined as a time that the falling body 50 passes through the intermediate position C1 in the vertical direction of the coils 3 and 4. Similarly, the time T6 of the intersecting point X2 is defined as a time that the falling body 50 passes through the intermediate position C2 in the vertical direction of the coils 5 and 6.

As shown in FIG. 3, the passing time T7 required from the time T5 to the time T6 is defined based on the intersecting point X1 (T5, V0) and the intersecting point X2 (T6, V0) which are obtained as described above. The passing time T7 is obtained by a calculation for subtracting the time T5 from the time T6 in accordance with a program. The passing time T7 can be defined as a time required for the falling body 50 to pass from the intermediate position C1 in the vertical direction of the coils 3 and 4 (see FIG. 1) to the intermediate position C2 in the vertical direction of the coils 5 and 6 (see FIG. 1).

As described above, it is possible to obtain the passing time T7 (see FIG. 3) required for the falling body 50 to pass through the specified distance L between the coils 3 and 4 (the intermediate position C1) and the coils 5 and 6 (the intermediate position C2) as shown in FIG. 1. It is assumed that the specified distance L is previously input to the arithmetic and control unit 10 (the storing portion 13) (see FIG. 2). By dividing the specified distance L by the passing time T7, it is possible to calculate the falling speed v of the falling body 50 (the falling speed v (mm/msec)=L (mm)/T7 (msec)). The falling speed v is calculated by utilizing the passing time T7 obtained based on the intersecting point X1 (T5, V0) and the intersecting point X2 (T6, V0) which are minimally influenced by noise as shown in FIG. 3. On the same measuring condition, therefore, a variation in a result of the measurement is lessened so that it is possible to calculate the falling speed v with high accuracy in the measurement.

As described above, as shown in FIGS. 1 to 3 in the first example, there are defined:

a first time (the intersecting point X1 (the time T5)) between the time T1 that the maximum value M1 is taken and the time T2 that the minimum value M2 is taken in the electric potential of the first coil pair A which is generated in the passage of the falling body 50 through the first coil pair A at which a coincident electric potential with the reference voltage V0 generated between the coils 3 and 4 through the electric potential applied from the power supply to the first coil pair A is defined; and a second time (the intersecting point X2 (the time T6)) between the time T3 that the maximum value M3 is taken and the time T4 that the minimum value M4 is taken in the electric potential of the second coil pair B which is generated in the passage of the falling body 50 through the second coil pair B at which a coincident electric potential with the reference voltage V0 generated between the coils 5 and 6 through an electric potential applied from the power supply to the second coil pair B is defined, the time T7 required from the first time T5 to the second time T6 is defined as the passing time T7 required for a passage through the specified distance L, and the falling speed v of the falling body is defined based on the passing time T7 and the specified distance L.

By utilizing the falling speed v, it is possible to obtain a viscosity μ of the measured substance 30 which has a small variation in a result of a measurement and high accuracy in the measurement. Referring to a method of calculating the viscosity μ using the falling speed v, it is possible to utilize the methods disclosed in Japanese Laid-Open Patent Publication No. 8-219973 and Japanese Laid-Open Patent Publication No. 2006-208260. By executing the methods disclosed in the publications in accordance with a program, it is possible to calculate the viscosity μ.

Figure 4:
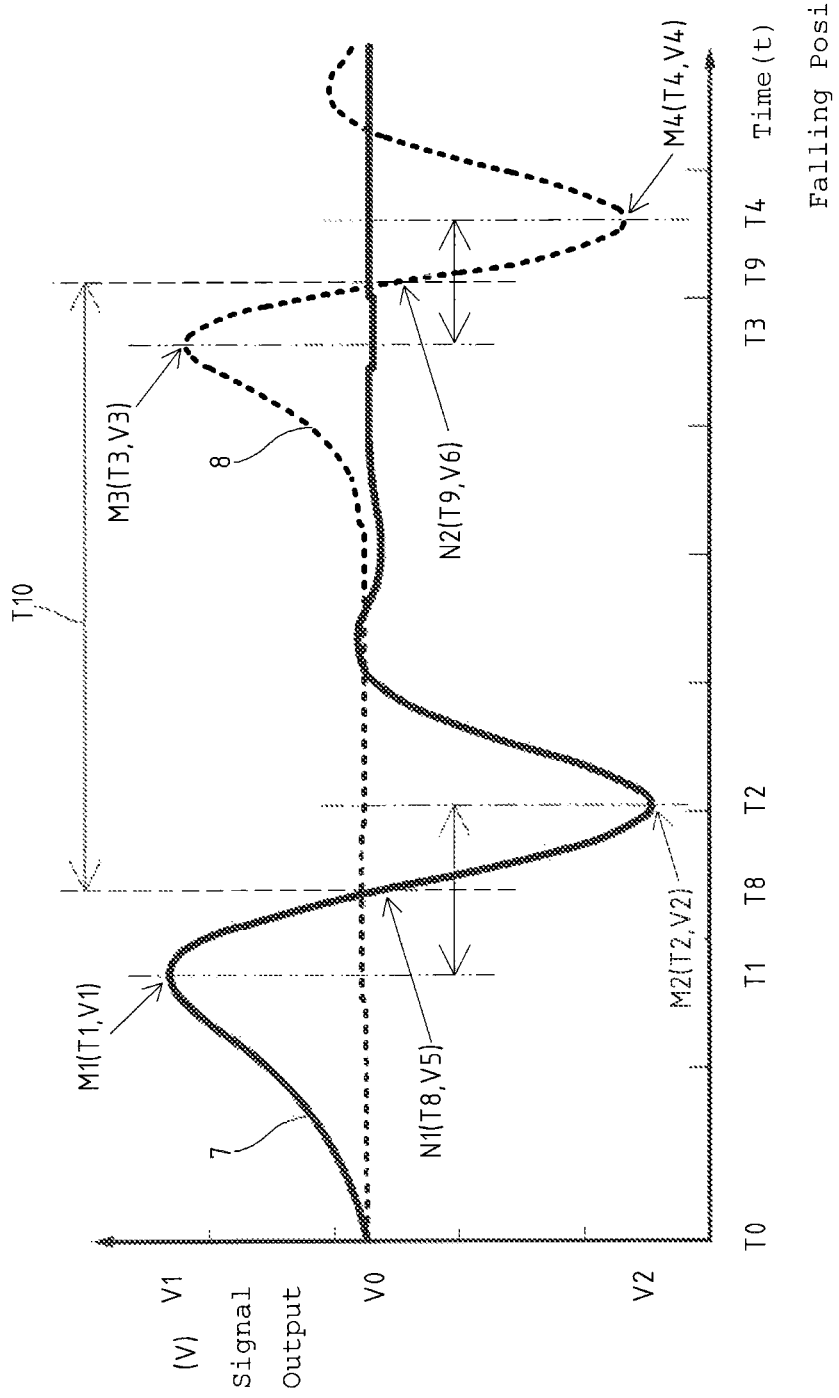
FIG. 4 is a chart showing a second example for calculating the passing time based on the waveform of the signal output (V).

<Second Example: Example in which passing time T10 is defined based on intermediate value> Description will be given to an example in which the intermediate values N1 and N2 are obtained from the maximum values M1 and M3 and the minimum values M2 and M4 and a time between the intermediate values N1 and N2 is defined as the passing time T10 as shown in FIG. 4. The voltage V1 has a value which is defined based on a maximum value of the signal output (V) that is measured, and the time T1 is defined based on a value (the time (t)) of a counter when the voltage V1 is measured. Even if a noise is contained in the signal output (V), the time T1 that the maximum voltage V1 is measured for a measuring period can be set onto a single point. For the measuring period, therefore, it is possible to define the maximum value M1 (T1, V1). Similarly, the voltage V2 has a value which is defined based on a minimum value of the signal output (V) that is measured, and the time T2 is defined based on a value (the time (t)) of the counter when the voltage V2 is measured. Even if a noise is contained in the signal output (V), the time T2 that the minimum voltage V2 is measured for a measuring period can be set onto a single point. For the measuring period, therefore, it is possible to define the minimum value M2 (T2, V2).

Referring to the coils 5 and 6 shown in FIG. 2, similarly, it is possible to define two extreme values for the signal output (V), that is, the maximum value M3 (T3, V3) and the minimum value M4 (T4, V4) as in the waveform 8 illustrated in FIG. 4.

As shown in FIG. 4, the intermediate value N1 (T8, V5) at an intermediate time T8 between the times T1 and T2 is defined based on the maximum value M1 (T1, V1) and the minimum value M2 (T2, V2) for the waveform 7 obtained as described above. In other words, the time T8=(the time T2-the time T1)/2 is defined.

As shown in FIGS. 1 and 4, moreover, the intermediate time T8 can be regarded as a time that the falling body 50 passes through the intermediate position C1 in the vertical direction of the coils 3 and 4. Furthermore, it is possible to calculate the intermediate value N1 by storing information about the maximum value M1 (T1, V1) and the minimum value M2 (T2, V2) and obtaining the intermediate time T8 between the times T1 and T2 in accordance with a program, thereby acquiring a voltage V5 at the intermediate time T8. The calculation of the intermediate value N1 can be executed with the structure of the arithmetic and control unit 10 shown in FIG. 2.

As shown in FIG. 4, similarly, the intermediate value N2 (T9, V6) at an intermediate time T9 between the times T3 and T4 is defined based on the maximum value M3 (T3, V3) and the minimum value M4 (T4, V4) for the waveform 8. In other words, the time T9=(the time T4-the time T3)/2 is defined.

As shown in FIGS. 1 and 4, moreover, the intermediate time T9 can be regarded as a time that the falling body 50 passes through the intermediate position C2 (see FIG. 1) in the vertical direction of the coils 5 and 6. Furthermore, it is possible to calculate the intermediate value N2 by storing information about the maximum value M3 (T3, V3) and the minimum value M4 (T4, V4) and obtaining the intermediate time T9 between the times T1 and T2 in accordance with a program, thereby acquiring a voltage V6 at the intermediate time T9. The calculation of the intermediate value N2 can be executed with the structure of the arithmetic and control unit 10 shown in FIG. 2.

As shown in FIG. 4, the passing time T10 required from the intermediate time T8 to the intermediate time T9 is defined based on the intermediate value N1 (T8, V5) and the intermediate value N2 (T9, V6) which are obtained as described above. The passing time T10 is obtained by a calculation for subtracting the intermediate time T8 from the intermediate time T9 in accordance with a program. The passing time T10 can be defined as a time required for the passage of the falling body 50 from the intermediate position C1 (see FIG. 1) in the vertical direction of the coils 3 and 4 to the intermediate position C2 (see FIG. 1) in the vertical direction of the coils 5 and 6.

As described above, as shown in FIG. 1, it is possible to obtain the passing time T10 (see FIG. 4) required for the falling body 50 to pass through the specified distance L between the coils 3 and 4 (the intermediate position C1) and the coils 5 and 6 (the intermediate position C2). It is assumed that the specified distance L is previously input to the arithmetic and control unit 10 (the storing portion 13) (see FIG. 2).

By dividing the specified distance L by the passing time T10, it is possible to calculate the falling speed v of the falling body 50 (the falling speed v (mm/msec)=L (mm)/T10 (msec)). As shown in FIG. 4, the falling speed v is obtained by utilizing the passing time T10 calculated based on the intermediate value N1 (T8, V5) and the intermediate value N2 (T9, V6). On the same measuring condition, therefore, a variation in a result of the measurement is lessened so that it is possible to calculate the falling speed v having high accuracy in the measurement. Referring to the calculation of the passing time T10, even if a noise is randomly contained in the signal outputs (V) of the maximum values M1 and M3 and the minimum values M2 and M4 and times required for measuring the maximum values M1 and M3 and the minimum values M2 and M4 have a variation for the respective measurements, it is possible to relieve the variation by acquiring the intermediate values N1 and N2 and to suppress an influence of the noise in the definition of the passing time T10.

As described above, as shown in FIGS. 1, 2 and 4 in the second example, there are defined:
the first intermediate time T8 (the intermediate value N1) between the time that the maximum value M1 is taken and the time that the minimum value M2 is taken in the electric potential of the first coil pair A which is generated in the passage of the falling body 50 through the first coil pair A (the coils 3 and 4); and
the second intermediate time T9 (the intermediate value N2) between the time that the maximum value M3 is taken and the time that the minimum value M4 is taken in the electric potential of the second coil pair B which is generated in the passage of the falling body 50 through the second coil pair B (the coils 5 and 6),
a time required from the first intermediate time T8 (the intermediate value N1) to the second intermediate time T9 (the intermediate value N2) is defined as the passing time T10 required for the passage through the specified distance L, and the falling speed v of the falling body 50 is defined based on the passing time T10 and the specified distance L.

By utilizing the falling speed v, it is possible to obtain the viscosity $\mu$ of the measured substance 30 which has a small variation in a result of the measurement and high accuracy in the measurement. Referring to a method of calculating the viscosity $\mu$ using the falling speed v, it is possible to utilize the methods disclosed in the Japanese Laid-Open Patent Publication No. 8-219973 and the Japanese Laid-Open Patent Publication No. 2006-208260. By executing the methods disclosed in the publications in accordance with a program, it is possible to calculate the viscosity $\mu$.

Example 2

Figure 5:
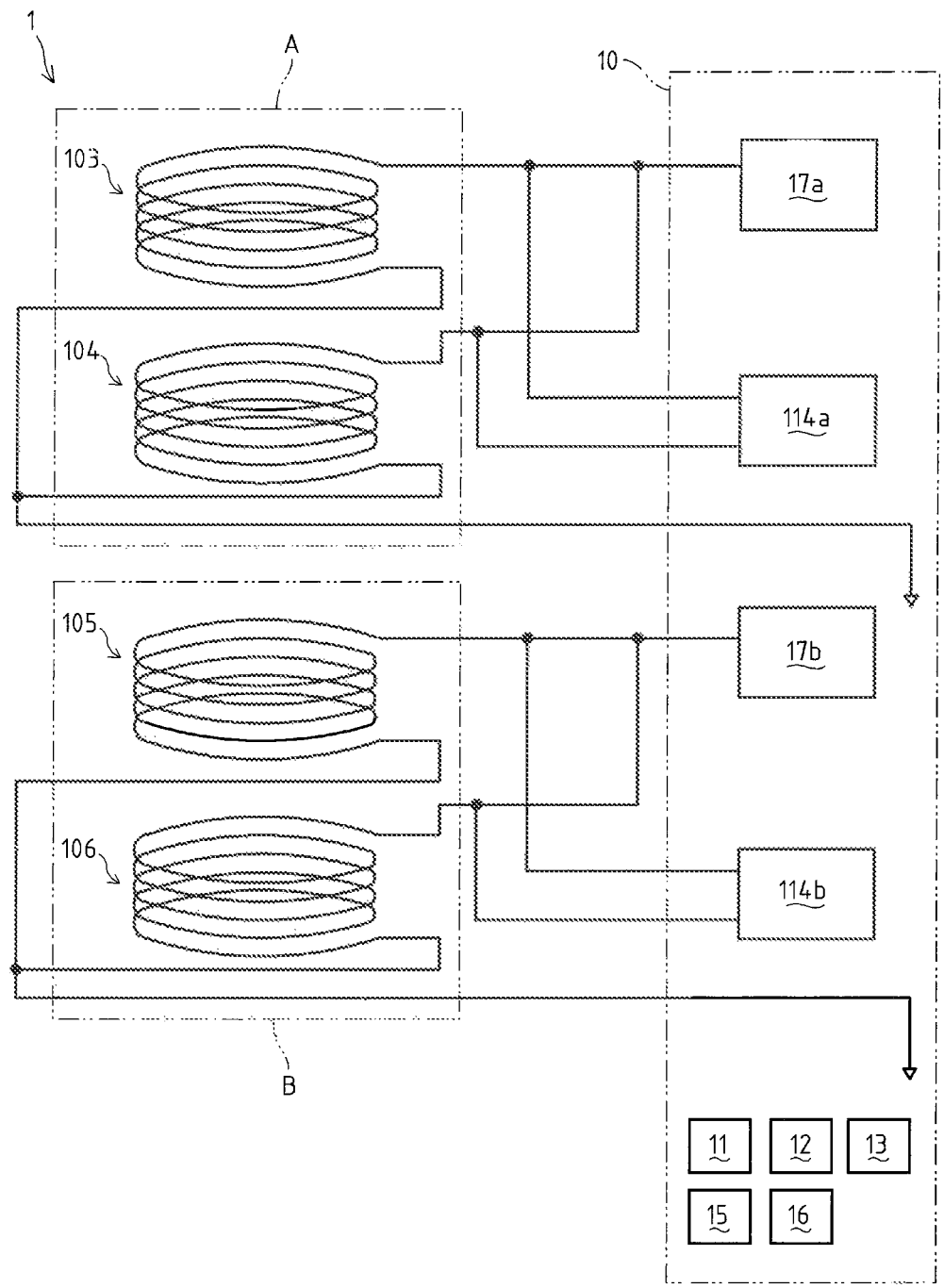
FIG. 5 is a view showing an arrangement of a coil constituting a falling speed measuring sensor according to an example 2 and a structure of an arithmetic and control unit.

Next, description will be given to an example in which the respective coil pairs A and B shown in FIG. 1 are arranged with the same polarity. As shown in FIG. 5, coils 103 and 104 are disposed in such a manner that polarities are identical to each other, that is, winding directions have an identical relationship, and they are connected in parallel. Similarly, coils 105 and 106 are also disposed in such a manner that polarities are identical to each other, that is, winding directions have an identical relationship, and they are connected in parallel.

As shown in FIG. 5, moreover, ends of the coils 103 and 104 and the coils 105 and 106 are connected to an arithmetic and control unit 10. The arithmetic and control unit 10 includes a CPU 11 for controlling the arithmetic and control unit 10 and a calculating portion 12 for carrying out a calculation based on a program to be executed by the CPU 11 and obtaining a voltage value, a time or the like for each of inverting positions Y1 and Y2 which will be described below. Moreover, the arithmetic and control unit 10 includes a storing portion 13 for storing the inverting positions Y1 and Y2 which will be described below, a falling speed of a falling body 50, a program for obtaining a viscosity of a measured substance 30, a signal output (V) which will be described below, and a time (t) that the signal output (V) is detected.

Furthermore, the arithmetic and control unit 10 includes amplifying portions 114a and 114b connected to the coils 103 and 104 and the coils 105 and 106 respectively and serving to amplify electric potentials generated over the coils 103 and 104 and the coils 105 and 106 and to output them as the signal output (V). In addition, the arithmetic and control unit 10 includes a counter 15 for defining the time (t) and outputting the time (t) to the storing portion 13. Moreover, the arithmetic and control unit 10 includes an output portion 16 for outputting a result of the calculation obtained by the calculating portion 12. Furthermore, the arithmetic and control unit 10 includes power supply portions 17a and 17b connected to the coils 103 and 104 and the coils 105 and 106 respectively and serving to apply predetermined magnetic fields. A constant current is supplied from the power supply portions 17a and 17b to the coils 103 and 104 and the coils 105 and 106, and constant electric potentials are generated over the coils 103 and 104 and the coils 105 and 106.

A characteristic structure shown in FIG. 5 includes the polarities (the winding directions) of the coils 103 and 104 and the coils 105 and 106, the supply of the current from the power supply portions 17a and 17b to the coils 103 and 104 and the coils 105 and 106, and the amplification and output of the electric potentials generated over the coils 103 and 104 and the coils 105 and 106 respectively in the amplifying portions 114a and 114b. Other embodiments can also be implemented by using other circuit structures and other apparatus structures and the present invention is not restricted to this structure. Moreover, it is also possible to carry out a connection to hardware such as a computer or a printer, thereby executing various analyzing operations or outputting a result.

Figure 6:
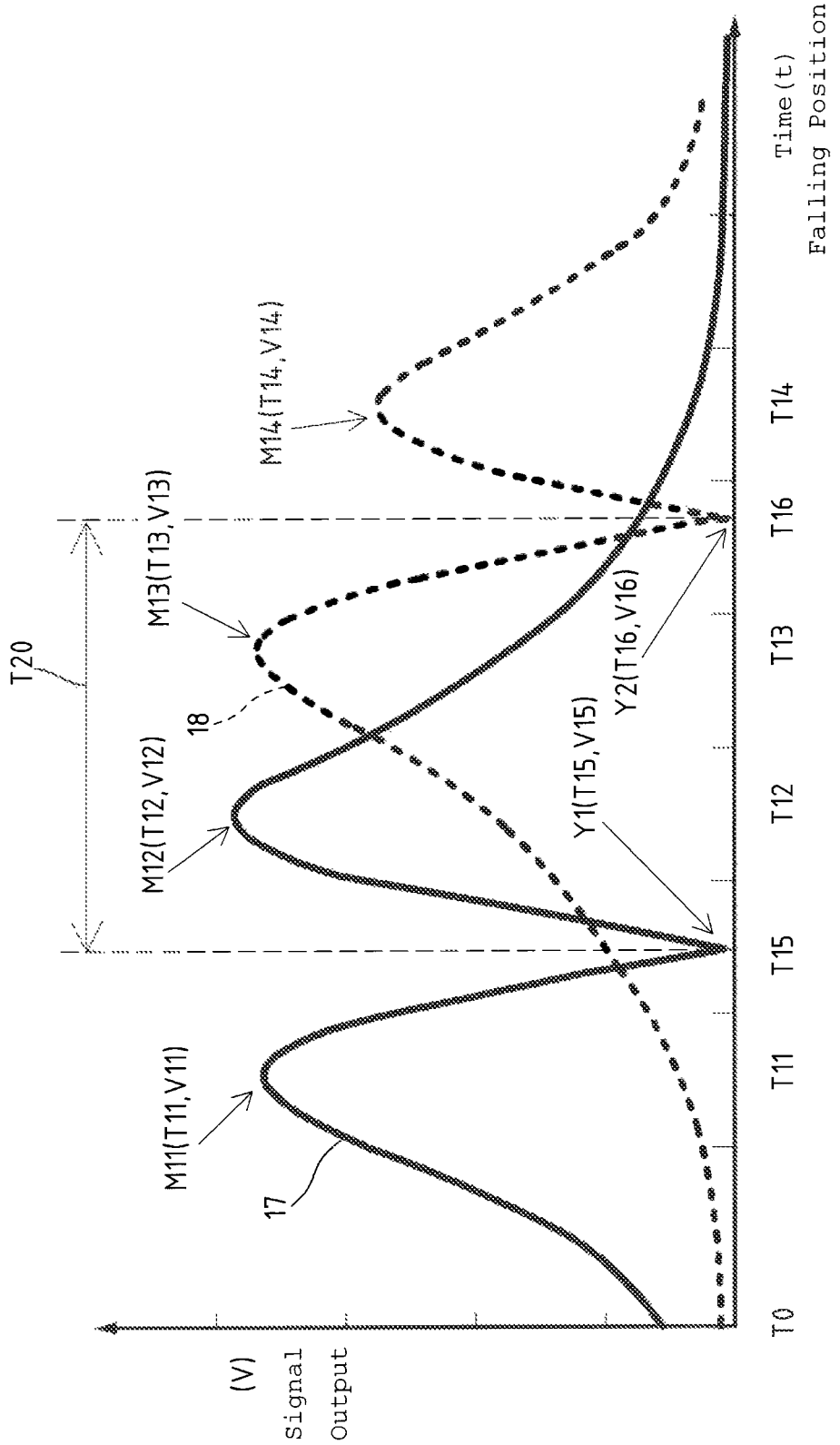
FIG. 6 is a chart showing a third example for calculating the passing time based on the waveform of the signal output (V).

By the structure described above, as shown in FIG. 6, it is assumed that the signal outputs (V) sent from the amplifying portions 114a and 114b (see FIG. 5) are obtained as waveforms 17 and 18. The electric potential in each of the coils 103 and 104 shown in FIG. 5 is amplified by the amplifying portion 114a, and the signal output (V) is sent as the waveform 17 making a transition with a passage of the time (t) as shown in FIG. 6 and is stored in the storing portion 13 (see FIG. 5). Similarly, the electric potential in each of the coils 105 and 106 shown in FIG. 5 is amplified by the amplifying portion 114b, and the signal output (V) is output as the waveform 18 making a transition with the passage of the time (t) as shown in FIG. 6 and is stored in the storing portion 13 (see FIG. 5). In FIG. 6, an axis of ordinate indicates the signal output (V) and an axis of abscissa indicates the time (t). Moreover, the axis of abscissa also corresponds to a falling position of the falling body.

First of all, as shown in FIG. 6, description will be given to the waveform 17 corresponding to the coils 103 and 104. The signal outputs (V) fluctuate with the time (t) respectively, and the signal output (V) takes a maximum value M11 at a time T11 and is then minimized at a time T15. Thereafter, the signal output (V) takes a maximum value M12 at a time T12 again. Thus, the signal output (V) is changed because an induced electromotive force is generated in the coils 103 and 104 respectively when the falling body 50 (see FIG. 1) approaches the coils 103 and 104, and the electric potentials of the coils 103 and 104 are thus varied by the induced electromotive force. By detecting a temporal change in the signal output (V) due to the induced electromotive force, it is possible to detect a positional relationship between the coils 103 and 104 and the falling body 50.

More specifically, in FIG. 6, the signal output (V) is increased from a reference voltage V0 to a voltage V11 when the falling body 50 approaches the coil 103 from a time T0 to the time T11. The reason is as follows. When the falling body 50 approaches the coil 103, an induced current is generated in the falling body 50 and a magnetic field created by the induced current acts on the coil 103 so that the electric potential in the coil 103 is changed. When the falling body 50 approaches the coil 104, moreover, the signal output (V) is increased up to a voltage V12. The reason is as follows. When the falling body 50 approaches the coil 104, a magnetic field produced by the induced current generated in the falling body 50 similarly acts on the coil 104 and a direction of the magnetic field is the same as that acting on the coil 103. In the same manner as the change in the electric potential in the coil 103, therefore, the electric potential in the coil 104 is varied. The amplifying portion 114a serves to output, as the serial waveform 17, the changes in the electric potentials generated in the coils 103 and 104 respectively.

As described above, on the assumption that the coils 103 and 104 are disposed to have the same polarity as shown in FIG. 5 and to continuously acquire the changes in the electric potentials of the coils 103 and 104, it is possible to obtain two extreme values for the signal output (V), that is, the maximum value M11 (T11, V11) and the maximum value M12 (T12, V12) as in the waveform 17 illustrated in FIG. 6. Referring to the coils 105 and 106 shown in FIG. 5, similarly, it is possible to obtain two extreme values, that is, a maximum value M13 (T13, V13) and a maximum value M14 (T14, V14) as in the waveform 18 illustrated in FIG. 6. Although the two maximum values M11 and M12 and the two maximum values M13 and M14 appear for the waveforms 17 and 18 respectively in the example, it is also possible to employ a structure in which two minimum values appear for each of the waveforms 17 and 18 depending on the winding direction of the coil.

<Third Example: Example in which passing time T20 is defined based on time for inversion of direction of change in electric potential> Next, description will be given to an example in which the inverting positions Y1 and Y2 present between the maximum values M11 and M12 and the maximum values M13 and M14 respectively are obtained and a time between the inverting positions Y1 and Y2 is defined as a passing time T20 as shown in FIG. 6 in the structure illustrated in FIG. 5. As shown in FIG. 6, the waveform 17 corresponds to the change in the electric potential in each of the coils 103 and 104, and the maximum value M11 (T11, V11) appears in the passage through the coil 103 and the maximum value M12 (T12, V12) appears in the passage through the coil 104 as described above. At a time T15 for a process from the maximum value M11 to the maximum value M12, a direction of the change in the electric potential is inverted. A point on which the change in the electric potential is inverted is defined as the inverting position Y1 (T15, V15).

As shown in FIG. 6, similarly, the waveform 18 corresponds to the change in the electric potential in each of the coils 105 and 106, and the maximum value M13 (T13, V13) appears in the passage through the coil 105 and the maximum value M14 (T14, V14) appears in the passage through the coil 106 as described above. At a time T16 for a process from the maximum value M13 to the maximum value M14, a direction of the change in the electric potential is inverted. A point on which the change in the electric potential is inverted is defined as the inverting position Y2 (T16, V16).

As shown in FIG. 6, the passing time T20 required from the time T15 to the time T16 is defined based on the inverting position Y1 (T15, V15) and the inverting position Y2 (T16, V16) which are obtained as described above. The passing time T20 is obtained by a calculation for subtracting the intermediate time T15 from the time T16 in accordance with a program. The passing time T20 can be defined as a time required for the falling body 50 to pass from the intermediate position C1 (see FIG. 1) in a vertical direction of the coils 103 and 104 to the intermediate position C2 (see FIG. 1) in a vertical direction of the coils 105 and 106.

As shown in FIG. 6, moreover, the inverting position Y1 and the inverting position Y2 are points on which the direction of the change in the electric potential of the signal output (V) is inverted, that is, the direction is switched to be right or reverse. Even if a noise is contained in the signal output (V), it is possible to define the inverting positions Y1 and Y2 without an influence of the noise. In other words, on the same measuring condition, it is possible to ensure high accuracy in the measurement of the passing time T20 required from the inverting position Y1 to the inverting position Y2.

As described above, it is possible to obtain the passing time T20 (see FIG. 6) required for the falling body 50 to pass through the specified distance L between the coils 103 and 104 (the intermediate position C1) and the coils 105 and 106 (the intermediate position C2) as shown in FIG. 1. It is assumed that the specified distance L is previously input to the arithmetic and control unit 10 (the storing portion 13) (see FIG. 5).

By dividing the specified distance L by the passing time T20, it is possible to calculate a falling speed v of the falling body 50 (the falling speed v (mm/msec)=L (mm)/T20 (msec)). The falling speed v is calculated by utilizing the passing time T20 obtained based on the two inverting positions Y1 (T15, V15) and Y2 (T16, V16) which are minimally influenced by noise as shown in FIG. 6. On the same measuring condition, therefore, a variation in a result of the measurement is lessened so that it is possible to calculate the falling speed v with high accuracy in the measurement.

As described above, as shown in FIGS. 1, 5 and 6 in the example, there are defined:
the first time T15 (the inverting position Y1) that the direction of the change in the electric potential is inverted in the electric potential of the first coil pair A (the coils 103 and 104) which is generated in the passage of the falling body 50 through the first coil pair A; and
the second time T16 (the inverting position Y2) that the direction of the change in the electric potential is inverted in the electric potential of the second coil pair B (the coils 105 and 106) which is generated in the passage of the falling body 50 through the second coil pair B,
a time required from the first time T15 (the inverting position Y1) to the second time T16 (the inverting position Y2) is defined as the passing time T20 required for the passage through the specified distance L, and the falling speed v of the falling body 50 is defined based on the passing time T20 and the specified distance L.

By utilizing the falling speed v, it is possible to obtain a viscosity μ of the measured substance 30 which has a small variation in a result of a measurement and high accuracy in the measurement. Referring to a method of calculating the viscosity using the falling speed v, it is possible to utilize the methods disclosed in the Japanese Laid-Open Patent Publication No. 8-219973 and the Japanese Laid-Open Patent Publication No. 2006-208260. By executing the methods disclosed in the publications in accordance with a program, it is possible to calculate the viscosity μ.

Figure 7:
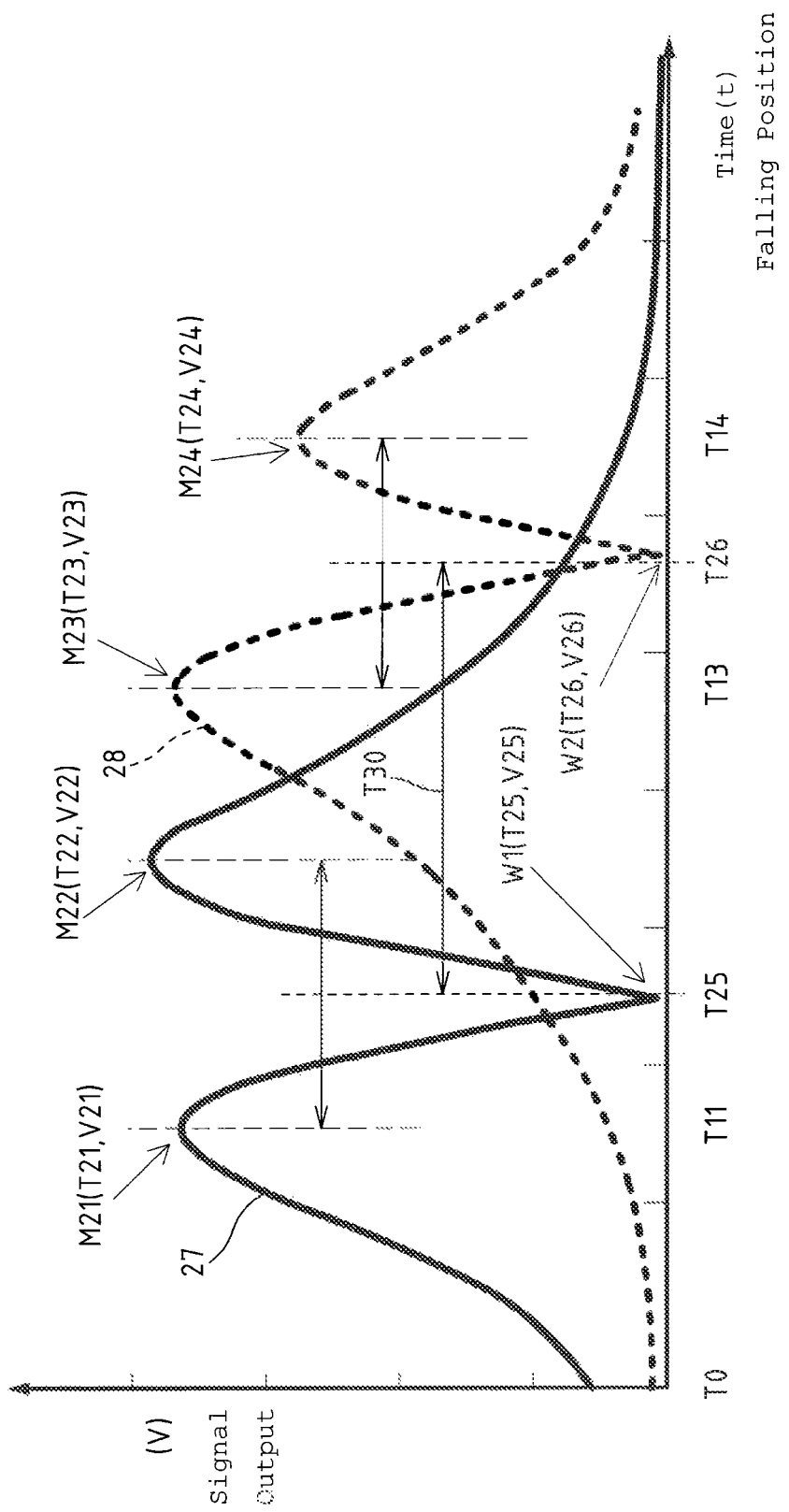
FIG. 7 is a chart showing a fourth example for calculating the passing time based on the waveform of the signal output (V).
Figure 8:
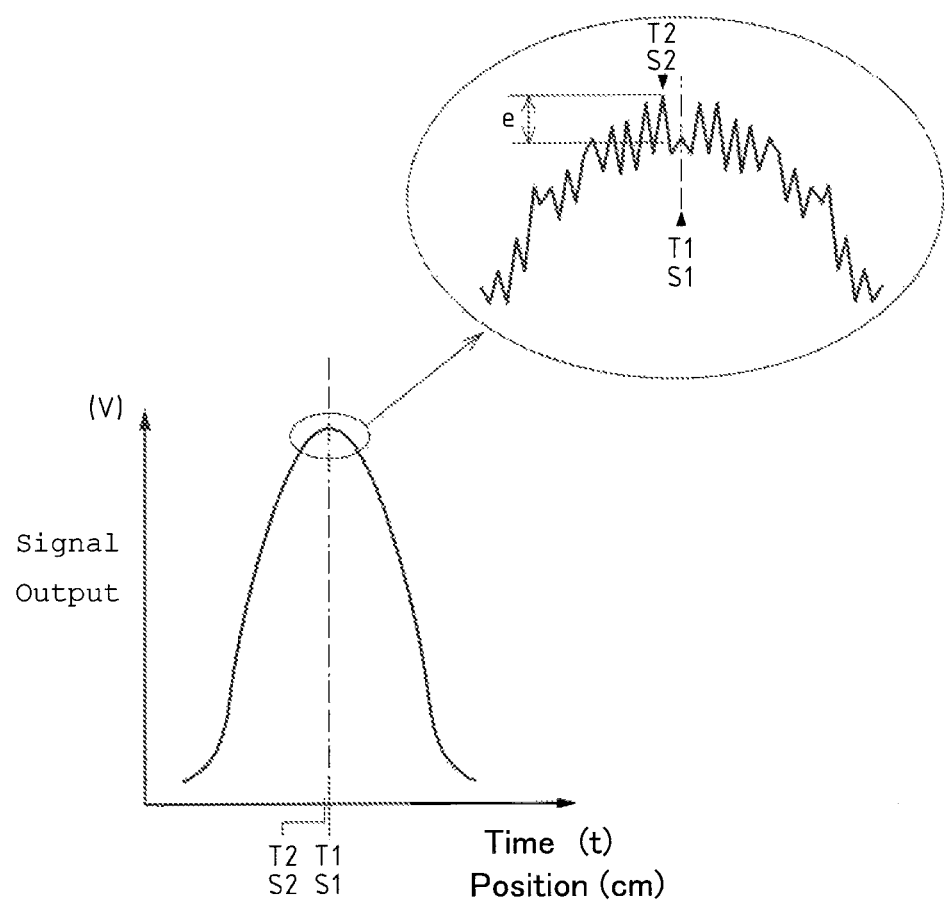
FIG. 8 is a chart showing a difficulty in specifying a position of an electromagnetic induction sensor using a coil.

<Fourth Example: Example in which passing time T30 is defined based on time having intermediate value of extreme value> Next, description will be given to an example in which intermediate values W1 and W2 present between maximum values M21 and M22 and maximum values M23 and M24 respectively are obtained and a time between the intermediate values W1 and W2 is defined as a passing time T30 as shown in FIG. 7 in the structure illustrated in FIG. 5. As shown in FIG. 7, a waveform 27 corresponds to the change in the electric potential in each of the coils 103 and 104, and the maximum value M21 (T21, V21) appears in the passage through the coil 103 and the maximum value M22 (T22, V22) appears in the passage through the coil 104 as described above. A point positioned in a middle of a time from the maximum value M21 to the maximum value M22 is defined as the intermediate value W1 (T25, V25). In other words, the intermediate time T25=(the time T22−the time T21)/2 is defined.

As shown in FIG. 7, similarly, a waveform 28 corresponds to the change in the electric potential in each of the coils 105 and 106, and the maximum value M23 (T23, V23) appears in the passage through the coil 105 and the maximum value M24 (T24, V24) appears in the passage through the coil 106 as described above. A point positioned in a middle of a time from the maximum value M23 to the maximum value M24 is defined as the intermediate value W2 (T26, V26). In other words, the intermediate time T26=(the time T24−the time T23)/2 is defined.

As shown in FIG. 7, the passing time T30 required from the intermediate time T25 to the intermediate time T26 is defined based on the intermediate value W1 (T25, V25) and the intermediate value W2 (T26, V26) which are obtained as described above. The passing time T30 is obtained by a calculation for subtracting the intermediate time T25 from the intermediate time T26 in accordance with a program. The passing time T30 can be defined as a time required for the falling body 50 to pass from the intermediate position C1 (see FIG. 1) in the vertical direction of the coils 103 and 104 to the intermediate position C2 (see FIG. 1) in the vertical direction of the coils 105 and 106.

As described above, as shown in FIG. 1, it is possible to obtain the passing time T30 (see FIG. 7) required for the falling body 50 to pass through the specified distance L between the coils 103 and 104 (the intermediate position C1) and the coils 105 and 106 (the intermediate position C2). It is assumed that the specified distance L is previously input to the arithmetic and control unit 10 (the storing portion 13) (see FIG. 5).

By dividing the specified distance L by the passing time T30, it is possible to calculate the falling speed v of the falling body 50 (the falling speed v (mm/msec)=L (mm)/T30 (msec)). As shown in FIG. 7, the falling speed v is obtained by utilizing the passing time T30 calculated based on the two intermediate values W1 (T25, V25) and W2 (T26, V26). On the same measuring condition, therefore, a variation in a result of the measurement is lessened so that it is possible to calculate the falling speed v having high accuracy in the measurement. Referring to the calculation of the passing time T30, even if a noise is randomly contained in the signal outputs (V) of the maximum values M21 and M22 and the maximum values M23 and M24 and times that the maximum values M21 and M22 and the maximum values M23 and M24 are measured have a variation for the respective measurements, it is possible to relieve the variation by acquiring the intermediate values W1 and W2 and to suppress an influence of the noise in the definition of the passing time T30.

As described above, as shown in FIGS. 1, 5 and 7 in the example, there are defined:

the first intermediate time T25 (the intermediate value W1) between the times that the maximum values M21 and M22 are taken in the electric potential of the first coil pair A (the coils 103 and 104) which is generated in the passage of the falling body 50 through the first coil pair A; and the second intermediate time T26 (the intermediate value W2) between the times that the maximum values M23 and M24 are taken in the electric potential of the second coil pair B (the coils 105 and 106) which is generated in the passage of the falling body 50 through the second coil pair B, the time required from the first intermediate time T25 (the intermediate value W1) to the second intermediate time T26 (the intermediate value W2) is defined as the passing time T30 required for the passage through the specified distance L, and the falling speed v of the falling body 50 is defined based on the passing time T30 and the specified distance L.

By utilizing the falling speed v, it is possible to obtain the viscosity μ of the measured substance 30 which has a small variation in a result of the measurement and high accuracy in the measurement. Referring to a method of calculating the viscosity in using the falling speed v, it is possible to utilize the methods disclosed in the Japanese Laid-Open Patent Publication No. 8-219973 and the Japanese Laid-Open Patent, Publication No. 2006-208260. By executing the methods disclosed in the publications in accordance with a program, it is possible to calculate the viscosity μ.

INDUSTRIAL APPLICABILITY

Various substances in which a falling body can fall by a deadweight, for example, blood, a beverage, a paint, chemicals, a yeast (a suspension or a muddy yeast), a food (a jelly food, a slurry-like food or the like), a yoghurt, a mayonnaise, a resin and the like may be the measured substance and thus a measuring target for a viscosity. In addition to a Newtonian fluid, moreover, the measured substance may be a substance classified as a non-Newtonian fluid. Referring to the measured substance, moreover, a viscosity μ can be measured for a specimen in a small quantity. In this respect, the invention particularly has advantages.

The invention claimed is:

1. A falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed, the falling speed measuring sensor comprising:

a first coil pair disposed on an outer periphery of the measuring container, separated from each other in a vertical direction, electrically connected in parallel, and provided to have different polarities from each other; and a second coil pair disposed on the outer periphery of the measuring container, separated from each other in the vertical direction, electrically connected in parallel, provided to have different polarities from each other, and arranged below the first coil pair by a specified distance, wherein the falling speed measuring sensor is configured to determine:

a first time between a time that a maximum value is taken and a time that a minimum value is taken in an electric potential generated continuously over both coils of the first coil pair in a passage of the falling body through the first coil pair at which there is defined a coincident electric potential with a reference voltage generated over the first coil pair by an electric potential applied from a power supply to the first coil pair;

a second time between a time that a maximum value is taken and a time that a minimum value is taken in an electric potential generated continuously over both coils of the second coil pair in a passage of the falling body through the second coil pair at which there is defined a coincident electric potential with a reference voltage generated over the second coil pair by an electric potential applied from the power supply to the second coil pair; and an elapsed time from the first time to the second time, wherein the elapsed time is a passing time taken for the falling body to pass through the specified distance.

2. A falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed, the falling speed measuring sensor comprising:

a first coil pair disposed on an outer periphery of the measuring container, separated from each other in a vertical direction, electrically connected in parallel, and provided to have different polarities from each other; and a second coil pair disposed on the outer periphery of the measuring container, separated from each other in the vertical direction, electrically connected in parallel, provided to have different polarities from each other, and arranged below the first coil pair by a specified distance, wherein the fallings speed measuring sensor is configured to determine:

a first intermediate time between a time that a maximum value is taken and a time that a minimum value is taken in an electric potential generated continuously over both coils of the first coil pair in a passage of the falling body through the first coil pair;

a second intermediate time between a time that a maximum value is taken and a time that a minimum value is taken in an electric potential generated continuously over both coils of the second coil pair in a passage of the falling body through the second coil pair; and an elapsed time from the first intermediate time to the second intermediate time, wherein the elapsed time is a passing time taken for the falling body to pass through the specified distance.

3. A falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed, the falling speed measuring sensor comprising:

a first coil pair disposed on an outer periphery of the measuring container, separated from each other in a vertical direction, electrically connected in parallel, and provided to have the same polarity; and a second coil pair disposed on the outer periphery of the measuring container, separated from each other in the vertical direction, electrically connected in parallel, provided to have the same polarity, and arranged below the first coil pair by a specified distance, wherein the falling speed measuring sensor is configured to determine:

a first time that a direction of a change in an electric potential of the first coil pair which is generated continuously over both coils of the first coil pair in a passage of the falling body through the first coil pair is inverted in the electric potential;

a second time that a direction of a change in an electric potential of the second coil pair which is generated continuously over both coils of the second coil pair in a passage of the falling body through the second coil pair is inverted in the electric potential; and an elapsed time from the first time to the second time, wherein the elapsed time is a passing time taken for the falling body to pass through the specified distance.

4. A falling speed measuring sensor for a falling body viscometer which is utilized in the falling body viscometer for causing a falling body to fall into a measured substance accommodated in a tubular measuring container, measuring a falling speed of the falling body by means of the falling speed measuring sensor, and measuring a viscosity of the measured substance by using the falling speed, the falling speed measuring sensor comprising:

a first coil pair disposed on an outer periphery of the measuring container, separated from each other in a vertical direction, electrically connected in parallel, and provided to have the same polarity; and a second coil pair disposed on the outer periphery of the measuring container, separated from each other in the vertical direction, electrically connected in parallel, provided to have the same polarity, and arranged below the first coil pair by a specified distance, wherein the falling speed measuring sensor is configured to determine:

a first intermediate time between times that extreme values are taken in an electric potential of the first coil pair which is generated continuously over both coils of the first coil pair in a passage of the falling body through the first coil pair;

a second intermediate time between times that extreme values are taken in an electric potential of the second coil pair which is generated continuously over both coils of the second coil pair in a passage of the falling body through the second coil pair; and an elapsed time from the first intermediate time to the second intermediate time, wherein the elapsed time is a passing time taken for the falling body to pass through the specified distance.

5. A falling body viscometer for causing a falling body to fall into a measured substance accommodated in a tubular measuring container, measuring a falling speed of the falling body by means of a falling speed measuring sensor, and measuring a viscosity of the measured substance by using the falling speed, the falling speed measuring sensor comprising:

a first coil pair disposed on an outer periphery of the measuring container, separated from each other in a vertical direction, electrically connected in parallel, and provided to have different polarities from each other; and a second coil pair disposed on the outer periphery of the measuring container, separated from each other in the vertical direction, electrically connected in parallel, provided to have different polarities from each other, and arranged below the first coil pair by a specified distance, wherein the first coil pair is configured to generate an electric potential continuously over both coils of the first coil pair, and wherein the second coil pair is configured to generate an electric potential continuously over both coils of the second coil pair.

6. A falling body viscometer for causing a falling body to fall into a measured substance accommodated in a tubular measuring container, measuring a falling speed of the falling body by means of a falling speed measuring sensor, and measuring a viscosity of the measured substance by using the falling speed, the falling speed measuring sensor comprising:
- a first coil pair disposed on an outer periphery of the measuring container, separated from each other in a vertical direction, electrically connected in parallel, and provided to have the same polarity; and
- a second coil pair disposed on the outer periphery of the measuring container, separated from each other in the vertical direction, electrically connected in parallel, provided to have the same polarity, and arranged below the first coil pair by a specified distance,
- wherein the first coil pair is configured to generate an electric potential continuously over both coils of the first coil pair, and
- wherein the second coil pair is configured to generate an electric potential continuously over both coils of the second coil pair.

7. A falling speed measuring method of causing a falling body to fall into a measured substance accommodated in a tubular measuring container and measuring a falling speed of the falling body, the method comprising:
- detecting a first maximum value and a first minimum value in an electric potential generated continuously over both coils of a first coil pair in a passage of the falling body through the first coil pair;
- defining a first time between a time of the first maximum value and a time of the first minimum value at which there is detected a coincident electric potential with a reference voltage generated over the first coil pair by an electric potential applied from a power supply to the first coil pair;
- detecting a second maximum value and a second minimum value in an electric potential generated continuously over both coils of a second coil pair in a passage of the falling body through the second coil pair;
- defining a second time between a time of the second maximum value and a time of the second minimum value at which there is detected a coincident electric potential with a reference voltage generated over the second coil pair by an electric potential applied from the power supply to the second coil pair;
- defining an elapsed time from the first time to the second time as a passing time taken for the falling body to pass through a specified distance; and
- defining the falling speed of the falling body based on the passing time and the specified distance,
- wherein the first coil pair is disposed on an outer periphery of the measuring container, separated from each other in a vertical direction, electrically connected in parallel, and provided to have different polarities from each other, and
- wherein the second coil pair disposed on the outer periphery of the measuring container, separated from each other in the vertical direction, electrically connected in parallel, provided to have different polarities from each other, and arranged below the first coil pair by the specified distance.

8. A falling speed measuring method of causing a falling body to fall into a measured substance accommodated in a tubular measuring container and measuring a falling speed of the falling body, the method comprising:
- detecting a first maximum value and a first minimum value in an electric potential generated continuously over both coils of a first coil pair in a passage of the falling body through the first coil pair;
- defining a first intermediate time between a time of the first maximum value and a time of the first minimum value;
- detecting a second maximum value and a second minimum value in an electric potential generated continuously over both coils of a second coil pair in a passage of the falling body through the second coil pair;
- defining a second intermediate time between a time of the second maximum value and a time of the second minimum value;
- defining an elapsed time from the first intermediate time to the second intermediate time as a passing time taken for the falling body to pass through a specified distance; and
- defining the falling speed of the falling body based on the passing time and the specified distance,
- wherein the first coil pair is disposed on an outer periphery of the measuring container, separated from each other in a vertical direction, electrically connected in parallel, and provided to have different polarities from each other, and
- wherein the second coil pair is disposed on the outer periphery of the measuring container, separated from each other in the vertical direction, electrically connected in parallel, provided to have different polarities from each other, and arranged below the first coil pair by the specified distance.

9. A falling speed measuring method of causing a falling body to fall into a measured substance accommodated in a tubular measuring container and measuring a falling speed of the falling body, the method comprising:
- detecting inversion of a change in direction of an electric potential of a then a first coil pair which is generated continuously over both coils of the first coil pair in a passage of the falling body through the first coil pair;
- defining a first time as a time of the inversion of the change in direction of the electric potential of the first coil pair;
- detecting inversion of a change in direction of an electric potential of a second coil pair which is generated continuously over both coils of the second coil pair in a passage of the falling body through the second coil pair;
- defining a second time as a time of the inversion of the change in direction of the electric potential of the second coil pair;
- defining an elapsed time from the first time to the second time as a passing time taken for the falling body to pass through a specified distance; and
- defining the falling speed of the falling body based on the passing time and the specified distance,
- wherein the first coil pair is disposed on an outer periphery of the measuring container, separated from each other in a vertical direction, electrically connected in parallel, and provided to have the same polarity, and
- wherein the second coil pair disposed on the outer periphery of the measuring container, separated from each other in the vertical direction, electrically connected in parallel, provided to have the same polarity, and arranged below the first coil pair by the specified distance.

10. A falling speed measuring method of causing a falling body to fall into a measured substance accommodated in a tubular measuring container and measuring a falling speed of the falling body, the method comprising:
- detecting first extreme values in an electric potential of a first coil pair which is generated continuously over both coils of coil pair in a passage of the falling body through the first coil pair;
- defining a first intermediate time between times that the first extreme values are detected;

detecting second extreme values in an electric potential of a second coil pair which is generated continuously over both coils of the second coil pair in a passage of the falling body through the second coil pair;

defining a second intermediate time between times that the second extreme values are detected;

defining an elapsed time from the first intermediate time to the second intermediate time as a passing time taken for the falling body to pass through a specified distance; and defining the falling speed of the falling body based on the passing time and the specified distance, wherein the first coil pair is disposed on an outer periphery of the measuring container, separated from each other in a vertical direction, electrically connected in parallel, and provided to have the same polarity, and wherein the second coil pair is disposed on the outer periphery of the measuring container, separated from each other in the vertical direction, electrically connected in parallel, provided to have the same polarity, and arranged below the first coil pair by the specified distance.

* * * * *

UNITED STATES PATENT AND TRADEMARK OFFICE
CERTIFICATE OF CORRECTION

PATENT NO. : 8,555,706 B2
APPLICATION NO. : 13/120978
DATED : October 15, 2013
INVENTOR(S) : Kimito Kawamura Page 1 of 1

It is certified that error appears in the above-identified patent and that said Letters Patent is hereby corrected as shown below:

In the specification:
In column 4, line 15: "a tabular measuring" should read --a tubular measuring--.

In column 10, line 66: "time W" should read --time (t)--.

In column 11, line 46: "the tabular measuring" should read --the tubular measuring--.

In column 18, lines 57–58: "viscosity using" should read --viscosity μ using--.

In column 20, line 20: "viscosity in using" should read --viscosity μ using--.

In the claims:
In column 21, line 30 (claim 2): "the fallings speed measuring" should read --the falling speed measuring--.

In column 24, line 31 (claim 9): "potential of a then a first" should read --potential of a first--.

In column 24, line 64 (claim 10): "coils of coil pair" should read --coils of the first coil pair--.

Signed and Sealed this
Seventh Day of January, 2014

Margaret A. Focarino
*Commissioner for Patents of the United States Patent and Trademark Office*